United States Patent [19]

Gerrard et al.

[11] Patent Number: 4,693,377
[45] Date of Patent: Sep. 15, 1987

[54] DIAMOND SEPARATION USING RAMAN SCATTERING

[75] Inventors: Donald L. Gerrard, Epsom; John E. Preedy, Bromley; Kenneth P. J. Williams, Camberley, all of England

[73] Assignee: The British Petroleum Company p.l.c., London, England

[21] Appl. No.: 902,092

[22] Filed: Aug. 27, 1986

Related U.S. Application Data

[63] Continuation of Ser. No. 611,740, May 18, 1984, abandoned.

[30] Foreign Application Priority Data

May 24, 1983 [GB] United Kingdom ............... 8314340

[51] Int. Cl.$^4$ ............................................. B07C 5/342
[52] U.S. Cl. .................................. 209/579; 209/644; 356/30; 356/301; 356/318; 364/498
[58] Field of Search ............... 209/576, 579, 587, 589, 209/644; 356/30, 301, 317, 318; 364/497, 498, 524, 525

[56] References Cited

U.S. PATENT DOCUMENTS

| | | | |
|---|---|---|---|
| 4,030,827 | 6/1977 | Delhaye et al. | 356/318 X |
| 4,057,146 | 11/1977 | Castaneda et al. | 209/586 X |
| 4,212,397 | 7/1980 | Bockelmann | 209/576 X |
| 4,620,284 | 10/1986 | Schnell et al. | 364/498 |

FOREIGN PATENT DOCUMENTS

| | | | |
|---|---|---|---|
| 0056513 | 7/1982 | European Pat. Off. | |
| 0071462 | 2/1983 | European Pat. Off. | |
| 2429624 | 2/1980 | France | 209/579 |
| 1379923 | 1/1975 | United Kingdom | |
| 1392466 | 4/1975 | United Kingdom | |
| 1407482 | 9/1975 | United Kingdom | |
| 1407481 | 9/1975 | United Kingdom | |
| 1528418 | 10/1978 | United Kingdom | |
| 2107861 | 5/1983 | United Kingdom | |
| 2073410 | 6/1984 | United Kingdom | |
| 0161703 | 4/1964 | U.S.S.R. | 209/589 |
| 0878369 | 11/1981 | U.S.S.R. | 209/576 |

Primary Examiner—Robert B. Reeves
Assistant Examiner—Edward M. Wacyra
Attorney, Agent, or Firm—Morgan & Finnegan

[57] ABSTRACT

A method for separating diamonds from gangue in which discrete units of gangue are passed through a beam of laser radiation capable of causing Raman spectral activation. The scattered radiation is detected and caused to actuate an ejector which separates units of diamond containing gangue from units of non-diamond containing gangue. The units of diamond containing gangue are then collected together.

7 Claims, 2 Drawing Figures

DIAMOND SEPARATION USING RAMAN SCATTERING

This is a continuation of co-pending application Ser. No. 611,740, filed May 18, 1984 now abandoned.

The present invention relates to a separation technique and more particularly relates to the separation of diamonds from associated waste material.

Diamond bearing ores unlike most other ores have a very low ratio of diamond to waste material (known as gangue) and it can be as little as one to several million. Further, the diamond must be recovered undamaged from the gangue and the presence of diamond in ores is not easily determined by chemical assay methods.

Diamonds occur in alluvial deposits or in kimberlite pipes. The ore is subjected to a series of mechanical enrichment processes involving sieving, crushing and density separation techniques to obtain a concentrate containing the diamonds and discarding the tailings or barren portion of the gangue. The material is then sized into a number of ranges by use of X-ray separators which detect the fluorescence of the diamond (and a number of other materials) causing an air ejection system to displace the diamond bearing fraction from the stream of material. The final selection of uncut diamonds is then made by hand.

The present invention relates to a technique for sensing diamond bearing material which is more selective than previous techniques and which lends itself to non-manual selection and thus enhances the security of the operation.

Thus according to the present invention there is provided a method for the separation of diamonds from a diamondiferous ore or gangue comprising the steps of (a) passing discrete units of gangue through a beam of laser radiation capable of causing Raman spectral activation, (b) detecting the scattered Raman radiation by means of a detector, (c) the detector being adapted to actuate means for separating discrete units of diamond containing ore from the discrete units of non-diamond containing ore, and (d) collecting the separated discrete units.

The invention also provides for concentrated diamondiferous material to be recycled through the separator at a different flow rate to enable further separation of the concentrated gangue.

The invention also includes a separator suitable for use in separating diamonds comprising a source of laser radiation, means for passing discrete units of a diamondiferous ore or gangue through the beam of the laser radiation, detecting means for detecting scattered Raman radiation and means for separating discrete units of high diamond content from the flow of small diamond content gangue, the separating means being triggered by the detecting means.

Preferably the detecting means comprises a diode analyser which is linked to a spectrometer. Preferably a computer based assessor or microprocessor decides whether the information received by the detecting means results from the radiation impinging on a diamond. The assessor is able to compare the information with pre-determined values of say the wavelength at which a spectral peak occurs, the peak size and the level above the background scatter. Preferably the assessor actuates a command system operating a separating means. The separating means preferably comprises an ejector capable of emitting a blast of compressed gas capable of displacing the discrete unit of gangue into an adjacent collector. The use of a narrow laser beam enables both large and small samples to be analyzed.

Conventional Raman spectrometers scan the scattered light, each wavelength being observed and measured sequentially. Using this scanning technique requires a time of the order of minutes to identify a specific substance such as a diamond. In the present invention it is preferred to use diode array detectors linked to an optical system, the arrays effectively comprising a series of detectors in line. This enables a large portion of the spectrum to be examined simultaneously and using this approach, a sample containing diamond can be identified in a time of the order tens of milliseconds or even faster. It is also preferred to collect the scattered radiation by use of an optical fibre system thereby enabling the detector and analysis system to be used remote from the diamond samples thereby enhancing the security and convenience of the separation process.

Although the method and separator are described as being used for the separation of diamonds from associated waste material, it is also envisaged that other precious stone, minerals or the like could be separated from associated material by the aforesaid method and separator.

The invention will now be described by way of example only and with reference to FIGS. 1 and 2 of the accompanying drawings.

A bowl feeder 2 contains diamondiferous ore or gangue (of particle size 8 to 1.5 mm) which has passed through an X-ray separator (not shown). The ore contains quartz, feldspar, corundum, a range of minerals which commonly include magnetite, ilmenite, garnets, epidates, zircon, calcite, kimberlite, granite, dionite and schists in addition to diamonds.

A conveyer 1 capable of passing the diamondiferous ore at a rate typically of about 6 cubic feet/day is linked to the bowl feeder 2 and leads to a gate separator 3 which is capable of dividing the continuous stream of ore into discrete units 4 for analysis. A possible arrangement is to have the conveyer in the form of a V-belt having a dimensioned slit at its base which enables the particles to be placed in a defined position for analysis.

Figure 1:
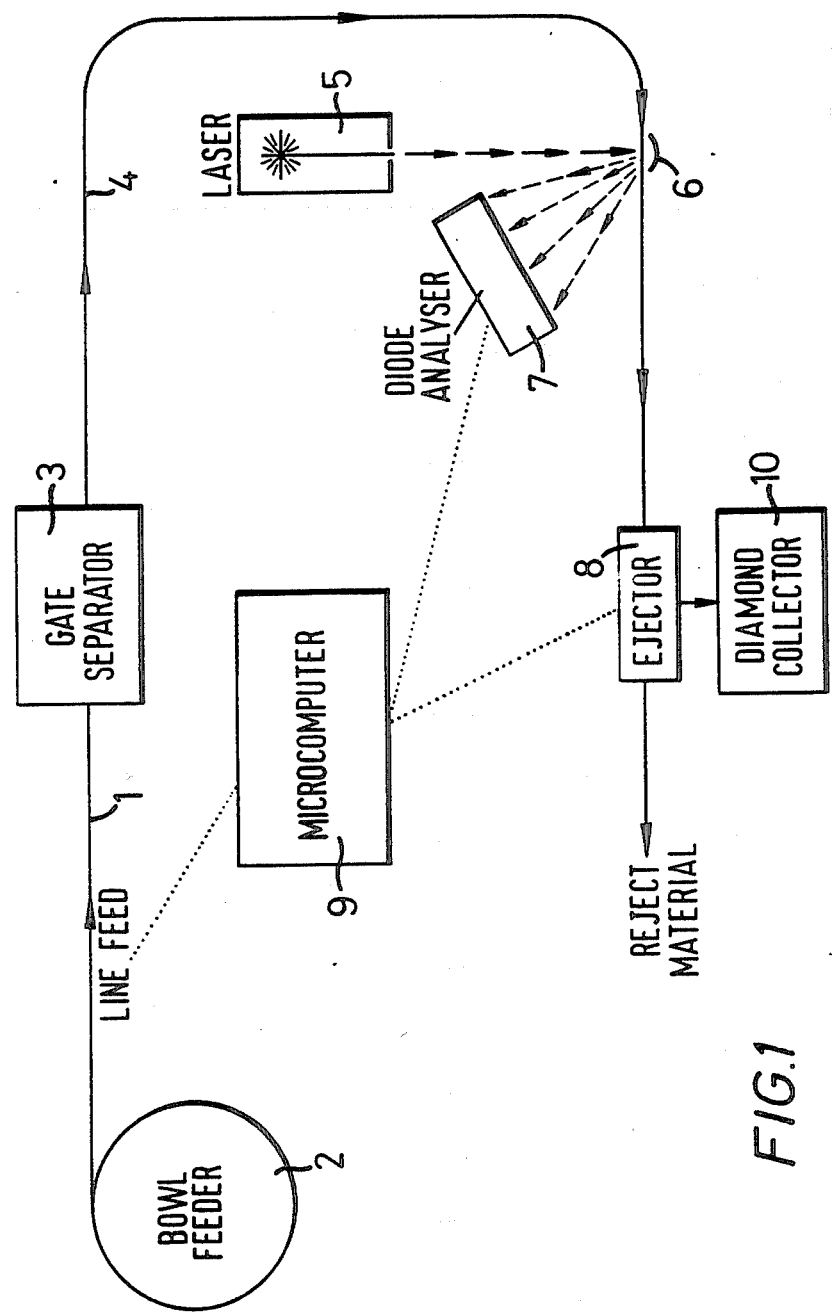
FIG. 1 is a schematic diagram of a diamond separator using the ore which has been partially refined by use of conventional techniques such as X-ray separation.
Figure 2:
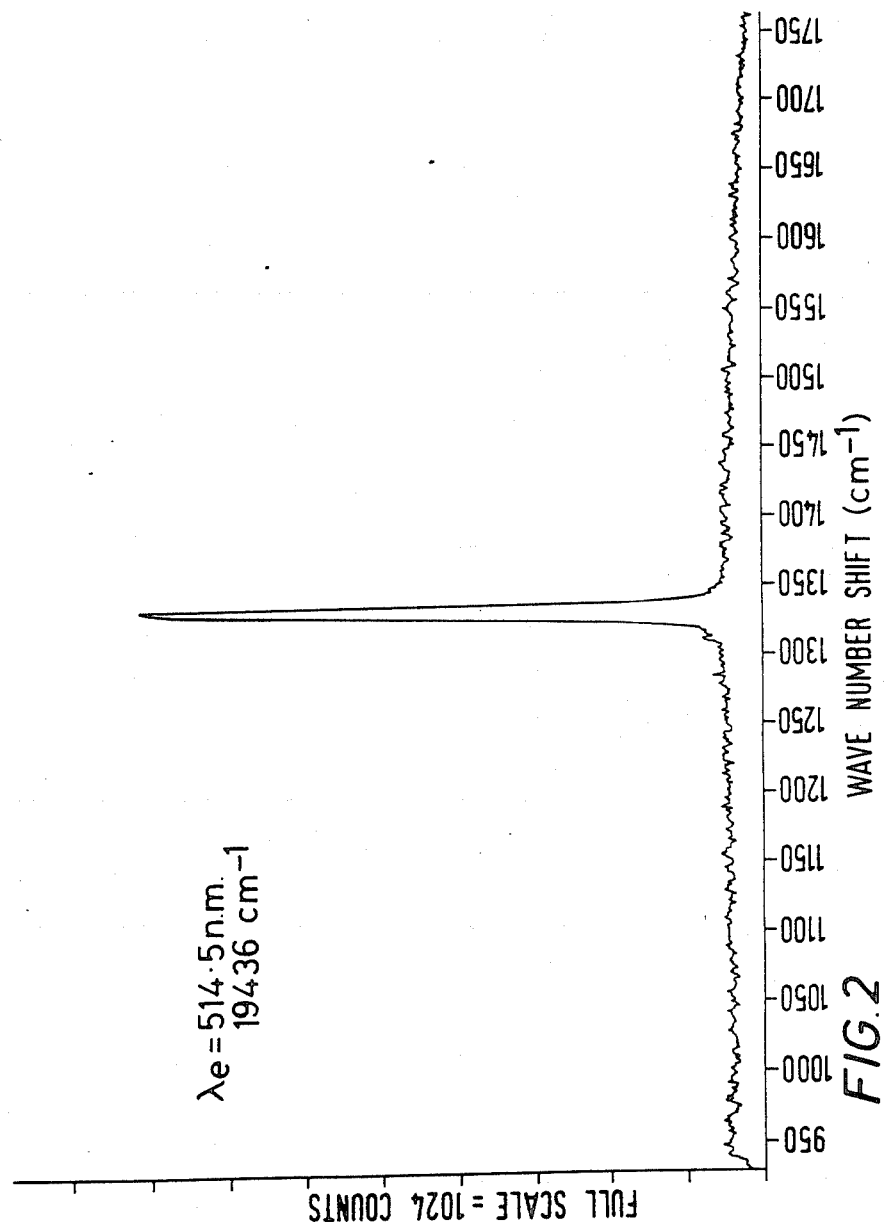
FIG. 2 is a typical Raman spectrum from a diamondiferous ore.

A continuous wave argon ion laser capable of delivering a high powered green (514.5 nanometers) exciting line is arranged to direct radiation at the end of the conveyor belt 1 so as to sample for diamonds just prior to the discrete units 4 of ore falling off the end of the belt 1. A collector 6 positioned behind the sample and remote from the radiation source 5 is capable of receiving the laser radiation scattered by the Raman effect. The collector 6 is linked (preferably by an optical fibre system) to a detector diode array 7 and a spectrometer. The diode array/spectrometer is capable of identifying a discrete unit comprising diamond in a time of the order tens of milliseconds. A typical diamond spectrum is shown in FIG. 2.

A compressed gas nozzle ejector 8 is located adjacent to and pointing at the current discrete unit being sampled. A microprocessor unit 9 linked to the detection system is capable of triggering the ejector 8 displace the diamond rich discrete units from the main ore stream into an adjacent collector 10.

The laser radiation may be taken to the conveyer belt by means of a fibre optic coupler accessory. The scattered Raman radiation is collected by a second fibre optic arrangement and is sent to the spectrometer. The collection optics housed within the spectrometer are able to focus the Raman radiation through the monochromator on to the diode array detector.

During use, the ore passing from the bowl feeder 2 onto the conveyor belt 1 is broken into discrete units or samples by the gate separator 3. As each unit reaches the end of the conveyor belt 1, laser radiation from the source impinges on it and the Raman scattered radiation is collected by the collector and detected by the diode array/spectrometer arrangement. Scattering caused by the laser radiation impinging on a diamond particle is sensed by the diode analyser 7 which by the action of a microprocessor 9, causes a puff of compressed gas to displace the diamond particle containing discrete unit of ore into an adjacent container 10. The non diamond containing discrete units of ore pass downwards unaffected by the ejector to a further container.

We claim:

1. A method for the separation of diamonds from a diamond containing ore comprising the steps of (a) passing the ore through a separator capable of dividing the ore into discrete units (b) shining a beam of laser radiation of known frequency onto successive discrete units of ore (c) filtering the Raman scattered radiation reflected from each discrete unit of ore by means of a filter adapted to remove all radiation except that characteristic of diamond and (d) passing the filtered radiation into a detector, the detector being adapted to actuate a separator capable of separating the units of diamond containing ore from the units of non-diamond containing ore.

2. A method according to claim 1 in which the discrete units of gangue are obtained by passing the gangue through a gate separator.

3. A method according to claim 1 or claim 2 in which the detector comprises a diode analyser adapted to receive laser radiation scattered by the gangue.

4. A method according to claim 1 in which the detector is linked to a computer based assessor capable of distinguishing spectral radiation scattered from diamond containing gangue.

5. A method according to claim 4 in which the assessor is capable of actuating the separating means.

6. A method according to claim 1 in which the separating means comprises an ejector using compressed gas to displace the discrete unit of gangue into an adjacent collector.

7. A method according to claim 1 in which the resultant separated diamond containing discrete units are recycled to enable further separation of the gangue.

* * * * *